United States Patent [19]

Michalczyk et al.

[11] 3,948,805

[45] Apr. 6, 1976

[54] CATALYSTS FOR CONVERTING MALEIC ANHYDRIDE TO γ-BUTYROLACTONE

[75] Inventors: Georg Michalczyk, Neukirchen-Vluyn; Karl-Heinz Gluzek, Alpen, both of Germany

[73] Assignee: Deutsche Texaco Aktiengesellschaft, Hamburg, Germany

[22] Filed: July 15, 1974

[21] Appl. No.: 488,352

[30] Foreign Application Priority Data
Aug. 3, 1973   Germany............................ 2339343

[52] U.S. Cl.............. 252/447; 252/455 R; 252/465; 252/466 B; 260/343.6
[51] Int. Cl.². B01J 21/18; B01J 29/06; B01J 23/16
[58] Field of Search .......... 252/454, 470, 474, 465, 252/455 R, 466 B, 447; 260/343.6

[56] References Cited
UNITED STATES PATENTS

| | | | |
|---|---|---|---|
| 3,113,138 | 12/1963 | Franko-Filipasic et al....... | 260/343.6 |
| 3,152,998 | 10/1964 | Moss................................... | 252/470 |
| 3,480,684 | 11/1969 | Hansford......................... | 252/465 X |
| 3,514,492 | 5/1970 | Juguin et al..................... | 252/454 X |
| 3,580,930 | 5/1971 | Miya et al........................ | 260/343.6 |
| 3,767,595 | 10/1973 | Montgomery...................... | 252/454 |
| 3,803,055 | 4/1974 | Reich................................. | 252/454 |

*Primary Examiner*—Carl F. Dees
*Attorney, Agent, or Firm*—T. H. Whaley; C. G. Ries; George J. Darsa

[57] ABSTRACT

A process for converting maleic anhydride to γ-butyrolactone by treating the anhydride with hydrogen in the presence of co-catalysts comprising palladium and nickel-copper chromite at elevated pressures and temperatures.

6 Claims, No Drawings

CATALYSTS FOR CONVERTING MALEIC ANHYDRIDE TO ALPHA-BUTYROLACTONE

BACKGROUND OF THE INVENTION

The invention relates to a process for converting maleic anhydride into γ-butyrolactone by treating the anhydride with hydrogen in the presence of co-catalysts comprising palladium and nickel-copper chromite at elevated pressure and temperature.

It is known to convert maleic anhydride consecutively into succinic acid, γ-butyrolactone and tetrahydrofuran by hydrotreatment. The difficulty is to obtain the particular desired product with maximum purity. While many catalysts have been proposed for the manufacture of γ-butyrolactone by hydrotreatment of maleic anhydride, the selectivity of the catalysts employed and the yields of γ-butyrolactone obtained leave room for improvement. Illustratively, U.S. Pat. No. 3,113,138 discloses a process wherein γ-butyrolactone is obtained by hydrotreating an anhydride using palladium on activated carbon as the catalyst. The principal disadvantage in this process is that it requires the use of a solvent from which the final or end product must be recovered.

It is the object of this invention to provide a process for converting maleic anhydride to γ-butyrolactone in high yields.

Another object of this invention is to provide a process for converting maleic anhydride to γ-butyrolactone in the presence of selective co-catalysts.

Yet another object of this invention is to provide a process wherein the removal of the solvent is no longer necessary and where high yields in γ-butyrolactone are obtained.

Other objects and advantages will become apparent from a reading of the following detailed description and examples.

DESCRIPTION OF THE INVENTION

Broadly, this invention contemplates a process for converting maleic anhydride into γ-butyrolactone by treating the anhydride with hydrogen in the presence of co-catalysts comprising palladium and nickel-copper chromite. Generally, the process is conducted under elevated pressures and at elevated temperatures. In one embodiment, maleic anhydride is dissolved in γ-butyrolactone and conversion of maleic anhydride is undertaken in the presence of a co-catalyst comprising a mixture of palladium on activated carbon and nickel-copper chromite deposited on an aluminum oxide base under conversion temperatures in the range of from 20° to 400°C., preferably from 100° to 250°C. and under pressures suitably of from 50 to 350 kg/cm², preferably 100 to 150 kg/cm².

The novel nickel-copper chromite catalyst employed as a co-catalyst comprises NiO, CuO and $Cr_2O_3$ deposited on an aluminum oxide base, for example eta or gamma alumina. Silica, such as kieselguhr, may also be present as a component of the catalyst. The mole ratio of NiO to CuO plus $Cr_2O_3$ is suitably in the range of about 1:0.1–5.0, preferably 1:0.7–1.8. Aluminum oxide as a component of the catalyst can be present in amounts ranging from about 5 to 50 weight percent. Silica can be present as a component in amounts ranging from 0 to 50 weight percent of the composite. When silica is present as a component, the aluminum oxide and silica together form from about 5 to about 60 weight percent of the nickel-copper chromite catalyst. The other co-catalyst, namely palladium, is known to the art of catalysis and suitably comprises the metal supported on a base such as carbon. In general, this catalyst comprises from about 0.1 to 10.0, preferably about 5, weight percent palladium supported on a carbon base.

According to a preferred embodiment of the process of this invention, hydrogen is introduced to a reactor containing maleic anhydride at a pressure of from 100 to 150 kg/cm², the temperature is raised to 100° to 250°C. within 2 hours, and subsequently the reaction os allowed to continue for 2 more hours. Shorter or longer periods of time can also be employed. While the amount of co-catalyst employed in the reaction can vary over a broad range, we employ from about 0.1 to 100, preferably about 6 to 10, parts by weight of the nickel-copper chromite catalyst per 100 parts by weight of maleic anhydride. The palladium catalyst is employed in the ratio of about 0.1 to 100, preferably 5 to 10, parts by weight of the nickel-copper chromite catalyst per 1 part by weight of palladium catalyst. A highly satisfactory weight ratio is 7 parts of nickel-copper chromite catalyst per 1 part of palladium catalyst where the palladium content of the resultant catalyst mixture amounts to, for example, 0.625 percent, determined by calculation. The catalyst amount and the proportions of the two catalysts relative to each other in the catalyst system may, of course, be varied over a wide range depending on the temperature and pressure conditions that have been selected for the process and the most appropriate co-catalyst ratio can be easily determined.

It was most surprising to find that the process is highly selective in forming γ-butyrolactone by the use of a nickel-containing copper chromite catalyst inasmuch as nickel-containing and cobalt-containing catalysts have previously been regarded as equivalent means for the conversion of maleic anhydride to γ-butyrolactone and tetrahydrofuran. It has now been found that by using a nickel-copper chromite catalyst in combination with a palladium catalyst, gamma-butyrolactone is obtained in high yields with only extremely small amounts of concomitant tetrahydrofuran. In addition, copper chromite catalyst as well as nickel catalysts are know to be quickly poisoned by acids and water, whereas the co-catalyst system of our invention comprising nickel-copper chromite and palladium is extremely resistant to water and carboxylic acids. Other advantages include long catalyst life and the co-catalysts are easily regenerated by heating with air at a temperature of from 200° to 500°C. and reducing with hydrogen at 150° to 450°C.

The nickel-copper chromite catalyst of our invention employed as a co-catalyst in the subject process as described above is prepared by admixing aluminum hydroxide with a salt of nickel and of copper, for example, the nitrate, chloride or salt of an organic acid, such as acetate and $CrO_3$ in an aqueous medium. Silica, such as kieselguhr, when desired can also be introduced to the mixture. After mixing the materials and separating water as, for example, by evaporation, the recovered mass is dried. The catalyst, after being ground, is calcined for about 1 to 5 hours at from about 250° to 500°C. suitably in an inert gaseous environment, such as argon, neon, helium and preferably nitrogen. subsequently, the catalyst is activated in a reducing environment, preferably in a stream of hydrogen, for 1 to 10 hours at 200° to 300°C. In a highly preferred procedure, the catalyst is calcined for approximately 3 hours at about 450°C. in a nitrogen stream and activated by contacting with a hydrogen stream for 3 hours at about 250°C. In addition to the composition of the catalyst it is the reducing environment and temperature that influences the catalyst activity.

In contrast to other processes for converting maleic anhydride to γ-butyrolactone which are conducted in the gaseous phase, the process of our invention is carried out in the liquid phase which is a great advantage with regard to conversion and reactor dimensions. The catalytic process can be conducted in a wide range of solvents inert to the reaction as, for example, aliphatic alcohols such as methanol, ethanol, butanol and higher alcohols; aromatics such as benzene, toluene or xylene; dimethylformamide; and cyclic ethers such as tetrahydrofuran or tetrahydropyran. A particularly preferred solvent for converting maleic anhydride is γ-butyrolactone which is the compound that emerges as the end product of the process and thus need not be removed. Whether γ-butyrolactone or another solvent is used in the course of the reaction, the results are the same. In general, the maleic anhydride concentration in the solvent can vary from 25 to 75 weight percent. When γ-butyrolactone is employed as solvent about 50 percent solutions are most convenient. In the instance where γ-butyrolactone is intended to be converted to tetrahydrofuran in a further stage, the reaction solvent for the maleic anhydride in such a case is preferably tetrahydrofuran.

The product of the instant process, γ-butyrolactone, has utility as a solvent and as a thinner for paints and lacquers. In addition, γ-butyrolactone is useful as an intermediate in the production of tetrahydrofuran.

In order to more fully illustrate the nature of our invention and the manner of practicing the same, the following examples are presented. In these examples, the best mode contemplated by us for carrying out our invention is set forth.

EXAMPLE 1

A nickel-copper chromite catalyst according to the invention was prepared as follows. 30.9 grams of aluminum-tri-secondary butylate were hydroylzed in hot water and the alcohol which formed was separated. Subsequently, 30.0 grams of $Cu(NO_3)_2 \cdot 3H_2O$ in 30 ml. of water, 31.6 grams of $CrO_3$ in 35 ml. of water, 112.8 grams of $Ni(NO_3)_2 \cdot 6H_2O$ in 150 ml. of water and 30.8 grams of kieselguhr were added and the material was kneaded for 1 hour. The water was evaporated from the material under vacuum and the material dried for 24 hours at a temperature of 110° to 120°C. The resultant catalyst mass was ground and calcined for 3 hours at 450°C. in a stream of nitrogen. After cooling to 200°C. a stream of hydrogen was introduced at a flow rate 33 liters per hour and the temperature raised at 250°C. within 1 hour. The activation was completed after 3 hours of hydrotreatment.

The catalyst had the following calculated composition in weight percent: 9.8 — CuO (0.123 mole), 24.0 — $Cr_2O_3$ (0.158 mole), 6.4 — $Al_2O_3$ (0.063 mole), 29.0 — NiO (0.388 mole) and 30.8 — $SiO_2$ (0.513 mole).

γ-Butyrolactone was prepared from maleic anhydride as follows. The reaction vessel consisted of a 1-liter stainless steel autoclave equipped with a stirrer. Two-hundred grams of maleic anhydride and 200 grams of γ-butyrolactone were mixed 2.5 grams of a 5 percent palladium on activated carbon powder catalyst in the presence of 17.5 grams of the nickel-copper chromite catalyst prepared above. The hydrogenation was performed at a hydrogen pressure of 100 kg/cm² until the pressure remained constant and the reaction temperature was raised from 20° to 250°C. in the course of 2 hours and maintained at this level for 2 hours. The gas-chromatographic analysis of the product showed 96 mole percent of γ-butyrolactone, 2.4 mole percent of tetrahydrofuran and 1.6 mole percent of succinic acid anhydride.

EXAMPLE 2

A nickel-copper chromite catalyst was prepared according to the following procedure. An aluminum hydroxide paste was obtained by hydrolyzing 179.5 grams of aluminum-tri-secondary butylate and admixing with a solution of 30.0 grams of $Cu(NO_3)_2 \cdot 3H_2O$ in 30 ml. of water, 31.6 grams of $CrO_3$ in 35 ml. of water and 112.8 grams of $Ni(NO_3)_2 \cdot 6H_2O$ in 150 ml. of water and kneaded for one hour. The catalyst was dried and activated according to the procedure of Example 1 and had the following composition: 9.8 — CuO (0.123 mole), 24.0 — $Cr_2O_3$ (0.158 mole), 37.2 — NiO (0.388 mole) and 29.0 — $Al_2O_3$ (0.365 mole).

γ-Butyrolactone was prepared from maleic anhydride in the following manner. 17.5 grams of the nickel-copper chromite catalyst prepared above and 2.5 grams of a 5 percent palladium on activated carbon catalyst were employed as co-catalysts for hydrogenating 200 grams of maleic anhydride in 200 grams of γ-butyrolactone under a hydrogen pressure of 100 kg/cm² at a temperature of 250°C. Analysis of the product showed 94.5 mole percent of γ-butyrolactone, 2.1 mole percent of tetrahydrofuran, 0.6 mole percent of propionic acid, 0.5 mole percent of butyric acid and 2.2 mole percent of succinic acid anhydride.

EXAMPLE 3

Another nickel-copper chromite catalyst was prepared according to the following procedure. To an aluminum hydroxide paste obtained by hydrolyzing 44.0 grams of aluminum-tri-secondary butylate there was added 40.7 grams of $Cu(NO_3)_2 \cdot 3H_2O$ in 45 ml. of water, 27.6 1 grams of $CrO_3$ in 30 ml. of water, 70.6 grams of $Ni(NO_3)_2 \cdot 6H_2O$ in 80 ml. of water and 38.5 grams of kieselguhr. The material was kneaded for 1 hour, dried and activated according to the procedure described in Example 1. The catalyst obtained had the following weight percent composition: 13.3 — CuO (0.167 mole), 21.0 — $Cr_2O_3$ (0.276 mole), 9.1 — $Al_2O_3$ (0.179 mole), 18.1 — NiO (0.243 mole) and 38.5 — $SiO_2$ (0.641 mole).

γ-Butyrolactone was prepared from maleic anhydride in the following manner. Four hundred grams of a 50 percent solution of maleic anhydride in γ-butyrolactone was hydrogenated in the presence of a mixture of 17.5 grams of the catalyst prepared as described above and 2.5 grams of a 5 percent palladium on activated carbon catalyst under a hydrogen pressure of 150 kg/cm² and at 250°C. Product analysis showed 96 mole percent of γ-butyrolactone and 4.0 mole percent of tetrahydrofuran.

EXAMPLE 4

Another nickel-copper chromite catalyst was prepared employing the following procedure. 176.2 grams of aluminum-tri-secondary butylate was hydrolyzed, and solutions of 46.1 grams of $Cu(NO_3)_2 \cdot 3H_2O$ in 50 ml. of water, 34.2 grams of $CrO_3$ in 40 ml. water and 87.6 grams $Ni(NO_3)_2 \cdot 6H_2O$ in 100 ml. water were added thereto. The mixture was kneaded and activated as described in Example 1. The catalyst obtained had the following composition on a weight percent basis: 15.2 — CuO (0.191 mole), 26.0 — $Cr_2O_3$ (0.342 mole), 36.3 — NiO (0.301 mole) and 22.5 — $Al_2O_3$ (0.365 mole).

γ-Butyrolactone was prepared from maleic anhydride as follows. 200 grams of maleic anhydride and 200 grams of γ-butyrolactone were hydrogenated in the presence of a co-catalyst composed of a mixture of 17.5 grams of the nickel-copper chromite catalyst prepared above and 2.5 grams of a 5 percent palladium on activated carbon at a pressure of 100 kg/cm² and at 250°C. A yield of 93.4 mole percent of γ-butyrolactone, 1.8 mole percent of tetrahydrofuran, 1.1 mole percent of propionic acid, 1.4 mole percent of butyric acid, and 2.3 mole percent of succinic acid anhydride was recovered.

As shown by the examples, the process of the invention leads to a 100 percent conversion of the maleic anhydride and the selectivity of the catalyst system for γ-butyrolactone ranges between 93.4 and 96 percent.

We claim:

1. A catalyst comprising nickel-copper chromite on aluminum oxide wherein the mole ratio of nickel as NiO to copper chromite as CuO and $Cr_2O_3$ ranges from about 1:0.1 to 1:5.0 and where said aluminum oxide is from 5 to 50 weight percent of said catalyst.

2. A catalyst according to claim 1 wherein said catalyst additionally comprises silica.

3. A catalyst according to claim 1 wherein the mole ratio of nickel as NiO to copper chromite as CuO and $Cr_2O_3$ ranges from about 1:0.7 to 1:1.8.

4. A catalyst according to claim 2 wherein said silica and aluminum oxide together comprise from about 5 to about 60 weight percent of said catalyst.

5. A co-catalyst comprising a mixture of 0.1 to 100 parts by weight of nickel-copper chromite on alumina catalyst according to claim 1 per 1 part by weight of a palladium catalyst.

6. A co-catalyst according to claim 5 wherein said palladium catalyst comprises from 0.1 to 10.0 weight percent palladium supported on a carbon base.

* * * * *